US010751218B2

(12) United States Patent
Blanchard et al.

(10) Patent No.: US 10,751,218 B2
(45) Date of Patent: Aug. 25, 2020

(54) AIR COOLED GOGGLE

(71) Applicant: 100% Speedlab, LLC, San Diego, CA (US)

(72) Inventors: Marc Blanchard, Solana Beach, CA (US); Ludovic Boinnard, San Diego, CA (US)

(73) Assignee: 100% Speedlab, LLC, San Diego, CA (US)

( * ) Notice: Subject to any disclaimer, the term of this patent is extended or adjusted under 35 U.S.C. 154(b) by 738 days.

(21) Appl. No.: 13/750,093

(22) Filed: Jan. 25, 2013

(65) Prior Publication Data
US 2014/0208489 A1    Jul. 31, 2014

(51) Int. Cl.
*A61F 9/02*    (2006.01)
(52) U.S. Cl.
CPC .................................... *A61F 9/028* (2013.01)
(58) Field of Classification Search
CPC .. A61F 9/02; A61F 9/028; A61F 9/026; A61F 9/025; A61F 9/027
USPC ............................ 2/436, 437, 426, 435, 439
See application file for complete search history.

(56) References Cited

U.S. PATENT DOCUMENTS

| | | | |
|---|---|---|---|
| 2,387,821 A * | 10/1945 | Baratelli et al. ......... | G02C 1/02 2/447 |
| 2,846,684 A | 8/1958 | Hill | |
| 3,368,221 A * | 2/1968 | Anderson ............... | A61F 9/025 2/437 |
| 3,517,393 A * | 6/1970 | Beauchef ............... | G02C 11/08 2/436 |
| 4,271,538 A | 6/1981 | Montesi et al. | |
| 4,425,669 A | 1/1984 | Grendol et al. | |
| 4,730,915 A | 3/1988 | Jannard | |
| 4,785,481 A * | 11/1988 | Palmer, III ................ | A61F 9/02 2/13 |
| 4,824,233 A | 4/1989 | Jannard | |
| 4,964,714 A | 10/1990 | Weymouth, Jr. et al. | |
| 4,977,627 A * | 12/1990 | Metcalfe ................. | A61F 9/028 2/437 |
| D330,903 S | 11/1992 | Jannard | |
| 5,239,320 A | 8/1993 | Allendorf et al. | |
| 5,363,512 A * | 11/1994 | Grabos, Jr. ............. | A61F 9/028 2/436 |
| D354,971 S | 1/1995 | Mugnier | |
| 5,379,464 A | 1/1995 | Schleger et al. | |
| D357,268 S | 4/1995 | Iida | |
| 5,444,876 A | 8/1995 | Cooper et al. | |

(Continued)

*Primary Examiner* — Anna K Kinsaul
*Assistant Examiner* — F Griffin Hall
(74) *Attorney, Agent, or Firm* — Kolitch Romano LLP

(57) ABSTRACT

A sports goggle comprising a lens attached to a flexible frame and configured to be positioned over the user's eyes, the flexible frame comprising an outer surface that is oriented away from the user's face and an inner surface that generally conforms to the shape of the user's face, the inner surface completely or partially covered with a flexible liner, and one or more first apertures in the outer surface connected to one or more apertures in the inner surface by one or more channels to allow airflow through the frame to the flexible liner. The flexible liner may be made of foam, open-cell foam, another porous material, or other material that allows air to pass through it. The goggle may include a screen and/or a filter positioned near the first aperture, between the first aperture and the second aperture, or near the second aperture.

17 Claims, 3 Drawing Sheets

(56) References Cited

U.S. PATENT DOCUMENTS

| | | | |
|---|---|---|---|
| 5,455,639 A | 10/1995 | Magdelaine et al. | |
| 5,517,700 A * | 5/1996 | Hoffman | A61F 9/028 2/428 |
| 5,519,896 A | 5/1996 | Ford | |
| D377,802 S | 2/1997 | Leonardi | |
| 5,610,668 A | 3/1997 | Mage | |
| 5,898,468 A | 4/1999 | Mage | |
| 6,029,271 A * | 2/2000 | Banuchi | A61F 9/04 2/12 |
| 6,076,196 A * | 6/2000 | Masumoto | A61F 9/028 2/436 |
| 6,138,285 A * | 10/2000 | Robrahn | A61F 9/028 2/434 |
| 6,196,676 B1 | 3/2001 | Tabacchi | |
| 6,227,664 B1 * | 5/2001 | Pavlak | A61F 9/026 2/437 |
| 6,257,719 B1 * | 7/2001 | Pavlak | A61F 9/026 2/437 |
| 6,481,845 B1 * | 11/2002 | Gazzara | A61F 9/026 2/436 |
| 6,513,171 B1 | 2/2003 | Soper | |
| 6,601,240 B2 * | 8/2003 | Tsubooka | A61F 9/028 2/436 |
| 6,611,966 B1 * | 9/2003 | Yamamoto | A61F 9/028 2/436 |
| 6,637,038 B1 | 10/2003 | Hussey | |
| 6,665,885 B2 * | 12/2003 | Masumoto | A61F 9/028 2/436 |
| D533,889 S | 12/2006 | Saderholm et al. | |
| 7,181,779 B2 * | 2/2007 | Hussey | A61F 9/027 2/426 |
| D542,829 S * | 5/2007 | Hsu | D16/312 |
| D546,868 S | 7/2007 | Teng | |
| D622,303 S | 8/2010 | Thixton | |
| 7,891,025 B2 * | 2/2011 | Kobayashi | A61F 9/028 2/436 |
| 8,303,109 B2 | 11/2012 | Matera | |
| D694,312 S | 11/2013 | Mage | |
| D711,960 S | 8/2014 | Mage et al. | |
| D727,398 S | 4/2015 | Blanchard et al. | |
| D727,400 S | 4/2015 | Blanchard et al. | |
| D756,446 S | 5/2016 | Yoo | |
| 2002/0023292 A1 * | 2/2002 | Masumoto | A61F 9/028 2/441 |
| 2003/0035082 A1 | 2/2003 | Olney | |
| 2005/0179856 A1 | 8/2005 | Van Atta et al. | |
| 2005/0183190 A1 * | 8/2005 | Hussey | A42B 3/185 2/424 |
| 2008/0013036 A1 | 1/2008 | Daems et al. | |
| 2008/0189838 A1 * | 8/2008 | Mage | A61F 9/02 2/436 |
| 2009/0077722 A1 | 3/2009 | Welchel et al. | |
| 2009/0188023 A1 | 7/2009 | Hsu | |
| 2010/0225879 A1 | 9/2010 | Pulito | |
| 2011/0258760 A1 * | 10/2011 | Renaud-Goud | A61F 9/027 2/431 |
| 2011/0279771 A1 | 11/2011 | Chen | |
| 2011/0296596 A1 * | 12/2011 | Chen | A61F 9/028 2/436 |
| 2012/0324638 A1 * | 12/2012 | Tobia | A61F 9/02 2/439 |
| 2013/0091623 A1 * | 4/2013 | McCulloch | A61F 9/025 2/435 |
| 2014/0063438 A1 | 3/2014 | Cater et al. | |
| 2014/0157496 A1 | 6/2014 | Ginther et al. | |
| 2014/0208489 A1 | 7/2014 | Blanchard et al. | |
| 2015/0074880 A1 * | 3/2015 | Blanchard | A61F 9/028 2/436 |

* cited by examiner

AIR COOLED GOGGLE

FIELD OF THE INVENTION

The invention relates generally to the field of sports goggles. In particular, the invention relates to managing airflow within and through a goggle frame.

DESCRIPTION OF RELATED ART

The prior art includes sports goggles used for a wide range of activities including motorcycle racing, snowboarding, skiing, BMX, and other activities where eye protection is critical while maintaining good visibility in a wide range of weather conditions. Prior art goggles have developed increasingly complex frames to create improved fit and flex characteristics and to allow the goggles to be used with a variety of different types of helmets. Prior art goggles have also attempted to manage airflow into the space behind the goggle lens to prevent fogging by providing smooth, laminar airflow across the back surface of the goggle lens. However, goggles are used in a wide range of weather conditions and one drawback to the use of prior art goggles is that they prevent natural air cooling of the skin area covered by the goggles.

The present invention overcomes this problem by providing a method and system for managing the flow of air through the frame of a modern sports goggle to disburse fresh air across areas where the goggle frame is in direct contact with the user's skin, cooling the user without introducing dust or other irritants into the eyes.

SUMMARY OF THE INVENTION

A sports goggle comprising a lens attached to a flexible frame and configured to be positioned over the user's eyes, the flexible frame comprising an outer surface that is oriented away from the user's face and an inner surface that generally conforms to the shape of the user's face, the inner surface completely or partially covered with a flexible liner, and one or more first apertures in the outer surface connected to one or more apertures in the inner surface by one or more channels to allow airflow through the frame to the flexible liner. In various exemplary embodiments, the flexible liner is made of foam, open-cell foam, another porous material, or other material that allows air to pass through it. In various exemplary embodiments, the goggle includes a screen positioned near the first aperture, between the first aperture and the second aperture, or near the second aperture. In various exemplary embodiments, the goggle includes a filter positioned near the first aperture, between the first aperture and the second aperture, or near the second aperture.

In various exemplary embodiments, an eye protection device includes a frame including an outer surface that is oriented away from a user's face and an inner surface that is oriented towards the user's face, wherein the frame includes a central raised portion disposed between a left portion and a right portion of a top portion of the frame; and the central raised portion extends vertically above a substantially continuous profile of the left and right portions. The eye protection device may include one or more first apertures in the outer surface connected to one or more apertures in the inner surface by one or more channels to allow airflow through the frame. The eye protection device may include a flexible liner completely or partially covering the top area and/or side areas of the inner surface of the frame, wherein the flexible liner is configured to be pressed against portions of the user's face. In various embodiments, the central raised portion may be joined to the left and right portions by corresponding left and right angled joints formed from the frame.

In various embodiments, the left and right angled joints include one or more first apertures in the outer surface connected to one or more apertures in the inner surface by one or more channels to allow airflow through the frame. In various embodiments, the frame includes a flexible polymer; and the inner surface includes a top area configured to conform generally to the shape of the user's forehead area and side areas configured to conform generally to the shape of the user's temples. In various embodiments, the frame includes side portions corresponding to the side areas of the inner surface of the frame: and the side portions of the frame are configured to couple to straps that are configured to hold the frame securely against the user's face. The eye protection device may include a lens attached to the frame and configured to be positioned over the user's eyes, wherein the lens includes a top edge corresponding to the top portion of the frame that is shaped to couple to the central raised portion and the left and right portions of the top portion of the frame. In various embodiments, the frame includes side portions corresponding to the side areas of the inner surface of the frame, the lens includes side edges corresponding to the side portion of the frame, and the side edges are shaped to couple to the side portions of the frame.

DETAILED DESCRIPTION OF THE PREFERRED EMBODIMENTS

Figure 1:
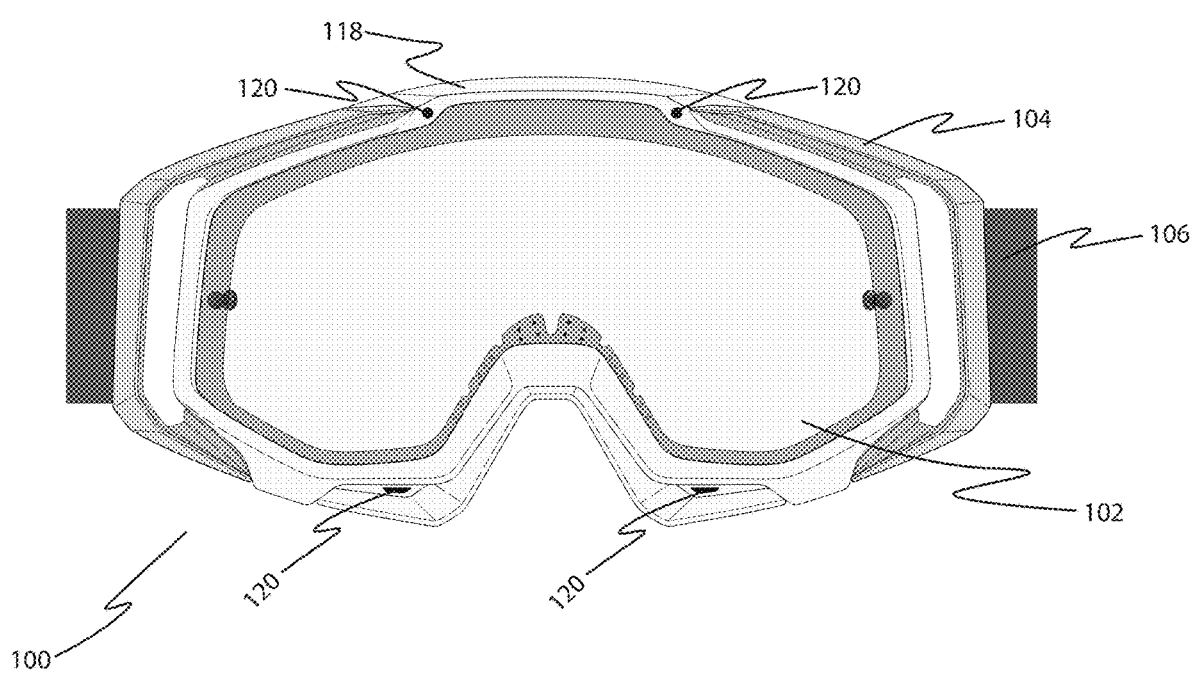
FIG. 1 is a diagram showing a front view of an exemplary embodiment of the present invention.

The following description is presented to enable any person skilled in the art to make and use the invention. For purposes of explanation, specific nomenclature is set forth to provide a thorough understanding of the present invention. Descriptions of specific embodiments or applications are provided only as examples. Various modifications to the embodiments will be readily apparent to those skilled in the art, and general principles defined herein may be applied to other embodiments and applications without departing from the spirit and scope of the invention. Moreover, in the present disclosure, various devices are described and set forth with regard to several embodiments. It is contemplated that features of the disclosed embodiments may be combined in any manner as may be desired for various applications and implementations. Thus, the present invention is not intended to be limited to the embodiments shown, but is to be accorded the widest possible scope consistent with the principles and features disclosed herein.

Referring to FIGS. 1 through 5, in various exemplary embodiments the invention comprises a goggle 100 generally comprising a lens 102, mounted in a frame 104 and a strap 106 to hold the frame 104 and lens 102 securely against the user's face. Frame 104 is commonly made of a flexible polymer and includes an inner surface 108 that is shaped to conform to the user's face. This inner surface 108 is covered by a liner 110 such as a sheet of face foam to provide a comfortable seal against the user's face and help to absorb moisture such as perspiration. The frame 104 comprises a single central raised portion 135 disposed between and substantially equidistant from a left portion and a right portion of a top portion of the frame 104. The central raised portion 135 extends vertically above a substantially continuous profile of the left and right portions of the top portion of the frame 104.

The top area of inner surface 108 presses against the user's forehead area, the bottom area of inner surface 108 presses against the user's cheeks and across the user's nose, and the side areas of inner surface 108 press against the user's temples. Since the inner surface 108 is typically positioned behind the lens 102 and outer surface 118 of frame 104, inner surface 108 and liner 110 do not receive consistent airflow and thus may become a hot spot during exertion or in hot weather conditions that can cause discomfort and fogging issues.

Figure 2:
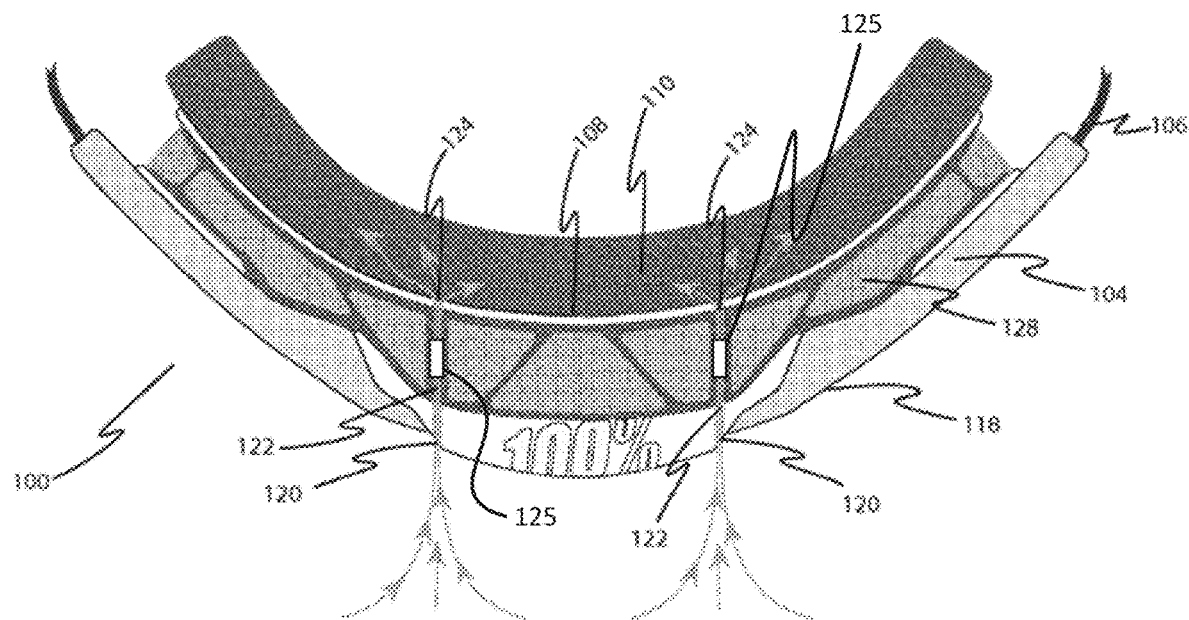
FIG. 2 is a diagram showing a top view of an exemplary embodiment of the present invention showing the air pathways through the frame of the goggle.
Figure 3:
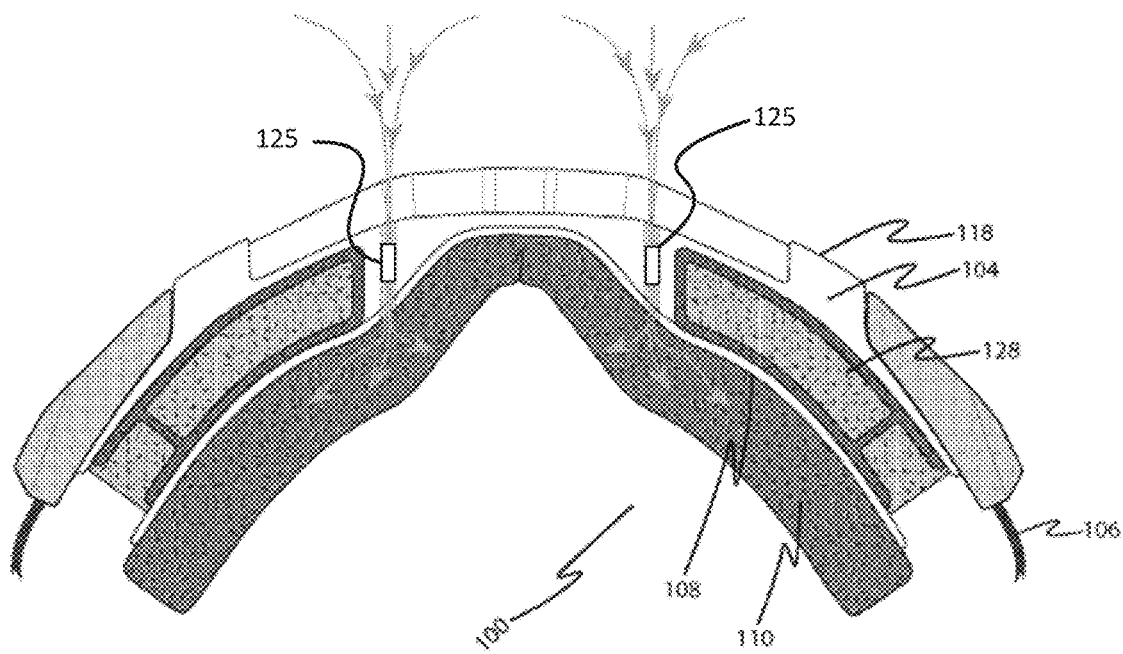
FIG. 3 is a diagram showing a bottom view of an exemplary embodiment of the present invention showing the air pathways through the frame of the goggle.
Figure 4:
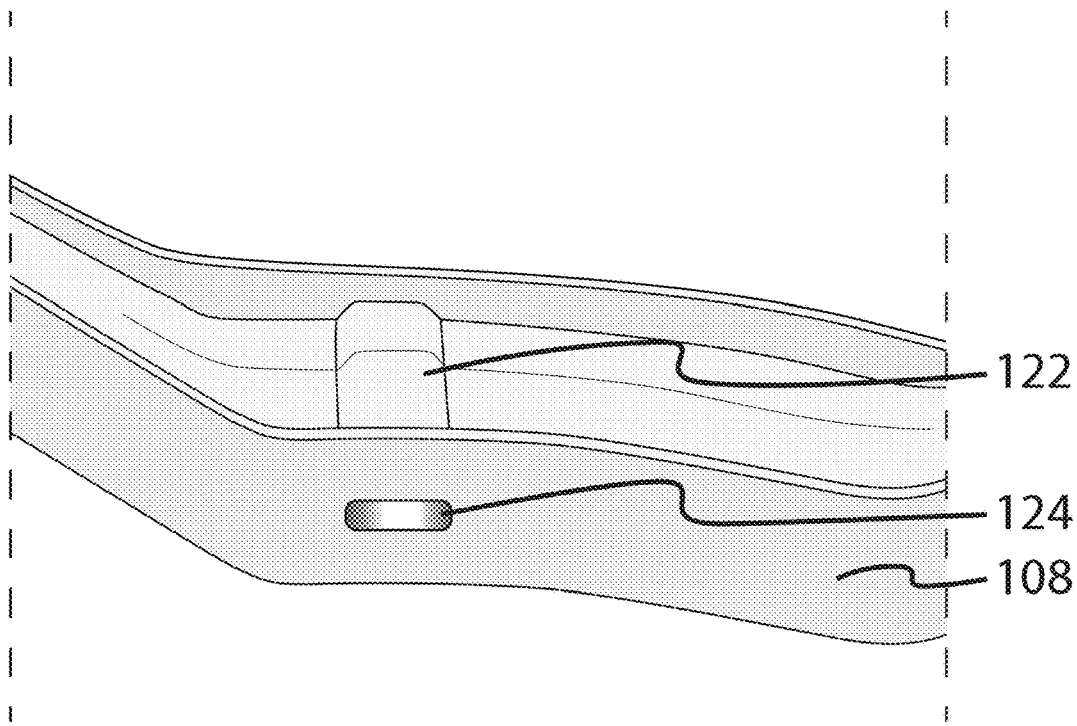
FIG. 4 is a diagram showing a section of the frame of an exemplary embodiment of the present invention.
Figure 5:
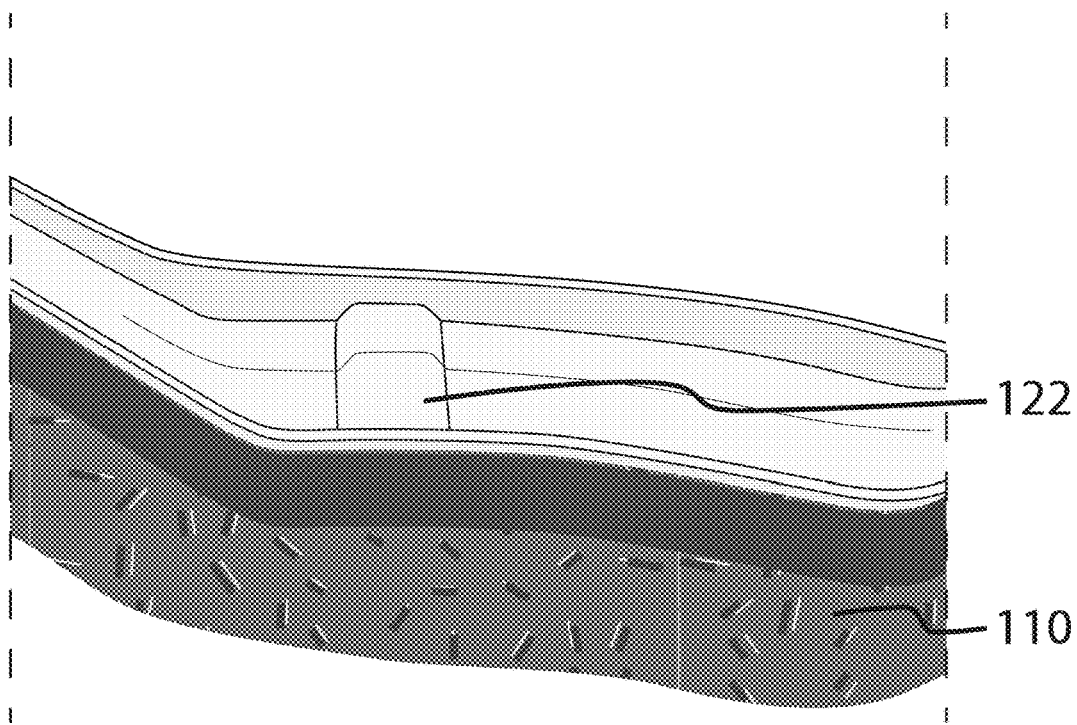
FIG. 5 is a diagram showing the same section of the frame of an exemplary embodiment of the present invention with foam positioned on the inner surface of the frame.

In an exemplary embodiment, one or more cooling vents are provided to manage airflow through the frame 104 so that it can be disbursed into the liner 110. In an exemplary embodiment, the cooling vents comprise first apertures 120 through the outer surface 118 of frame 104 that connect to channels 122 through the frame 104. These channels 122 connect to second apertures 124 through the inner surface 108. Thus, as illustrated in FIGS. 2 and 3, air flowing in through the first apertures 120 will pass along the channels 122 and through the second apertures 124, where it will be disbursed through the liner 110, cooling the liner 110 and the user's skin. Screens or other filters 125 can be placed in the first apertures 120, channels 122, or second apertures 124 as appropriate.

Because these cooling vents provide a direct channel to the liner 110, the incoming airflow is not disbursed into the space between the lens 102 and the user's eyes and portion of their face that is within the areas circumscribed by inner surface 108. Venting into that space is typically managed by various types of direct vents 128 that allow air to flow in and out through the frame 104.

It will be readily understood that the size, shape, configuration, and orientation of the cooling vents disclosed herein can be varied while still practicing the disclosed invention. For example, goggles designed for use in dusty environments such as motocross racing may have first apertures of a relatively small size to reduce the risk of taking in large quantities of dust and dirt. Goggles designed for uses such as snowboarding or skiing may have larger apertures and channels since dust is not a concern, but may utilize some type of closure mechanism to prevent cooling when the outside air is particularly cold. The shape and contours of the channels may also be varied to manage airflow through the frame.

What is claimed is:

1. A sports goggle comprising:
   a flexible frame comprising an outer surface and an inner surface, the outer surface configured to be oriented away from a user's face and the inner surface configured to conform to a shape of the user's face;
   a lens attached to the flexible frame, wherein the flexible frame is disposed at least partially around an outer periphery of the lens;
   a flexible liner provided on the inner surface of the flexible frame and configured to contact the user's face;
   a first aperture disposed on the outer surface of the flexible frame;
   a second aperture disposed on the inner surface of the flexible frame, wherein the flexible liner is disposed directly over the second aperture to cover the second aperture; and
   a channel extending through the flexible frame, connected to the first aperture and to the second aperture, and configured to direct airflow from the first aperture to the second aperture to disperse airflow flowing through the second aperture directly into the flexible liner to cool the user's face where the flexible liner contacts the user's face,
   wherein the flexible liner is configured to provide a seal against the user's face and the airflow directed from the first aperture to the second aperture through the channel is configured to cool the user's face where the flexible liner contacts the user's face when providing the seal, and
   wherein the flexible liner is configured to contact at least a forehead area, cheeks, and temples of the user to provide the seal.

2. The sports goggle of claim 1, wherein the flexible liner is made of foam that allows air to pass through it.

3. The sports goggle of claim 1, further comprising a screen positioned near at least one of the second apertures.

4. The sports goggle of claim 1, further comprising a filter positioned within the channel.

5. The sports goggle of claim 1, further comprising a plurality of the first apertures disposed on the outer surface, a corresponding plurality of the second apertures disposed on the inner surface, and a corresponding plurality of the channels formed through the flexible frame, wherein each channel is associated with a first aperture and a corresponding second aperture, and wherein the flexible liner is disposed directly over the plurality of the second apertures.

6. The sports goggle of claim 5, wherein at least one first aperture, second aperture, and channel is disposed on a top portion of the flexible frame, and wherein at least one first aperture, second aperture, and channel is disposed on a bottom portion of the flexible frame.

7. An eye protection device comprising:
   a frame comprising an outer surface and an inner surface, the outer surface configured to be oriented away from a user's face and the inner surface configured to be oriented towards the user's face, wherein:
   the frame is configured to receive a lens, wherein the frame is disposed at least partially around an outer periphery of the lens;
   the frame comprises a single central raised portion disposed between and substantially equidistant from a left portion and a right portion of a top portion of the frame, the central raised portion joined to the left and right portions by corresponding left and right angled joints formed from the frame; and
   the central raised portion extends vertically above a substantially continuous profile of the left and right portions of the top portion of the frame, wherein the frame further comprises:
   a flexible liner provided on the inner surface of the frame and configured to contact the user's face;
   a first aperture formed on the outer surface;

a second aperture formed on the inner surface, wherein the flexible liner is disposed directly over the second aperture to cover the second aperture; and a channel extending through the frame, connected to the first aperture and to the second aperture, to direct airflow from the first aperture to the second aperture to disperse airflow flowing through the second aperture directly into the flexible liner to cool the user's face where the flexible liner contacts the user's face, and the left and right angled joints comprise one or more first apertures in the outer surface connected to one or more second apertures in the inner surface by one or more channels to allow airflow through the frame.

8. The eye protection device of claim 7, wherein the flexible liner completely or partially covers a top area and/or side areas of the inner surface of the frame, and wherein the flexible liner is configured to be pressed against portions of the user's face to provide a seal against the user's face.

9. The eye protection device of claim 7, wherein:
the frame comprises a flexible polymer; and
the inner surface comprises a top area configured to conform generally to a shape of the user's forehead area and side areas configured to conform generally to a shape of the user's temples.

10. The eye protection device of claim 9, wherein:
the frame comprises side portions corresponding to the side areas of the inner surface of the frame; and
the side portions of the frame are configured to couple to straps that are configured to hold the frame securely against the user's face.

11. The eye protection device of claim 7, further comprising the lens attached to the frame and configured to be positioned over the user's eyes, wherein:
the lens comprises a top edge corresponding to the top portion of the frame that is shaped to couple to the central raised portion and the left and right portions of the top portion of the frame.

12. The eye protection device of claim 11, wherein:
the frame comprises side portions corresponding to side areas of the inner surface of the frame;
the lens comprises side edges corresponding to the side portions of the frame; and
the side edges are shaped to couple to the side portions of the frame.

13. The sports goggle of claim 1, wherein the flexible frame comprises a plurality of frame members extending between the outer surface and the inner surface.

14. The sports goggle of claim 13, wherein the plurality of frame members defines one or more vents allowing air to flow through the flexible frame.

15. The sports goggle of claim 14, wherein the channel extends through at least one of the one or more vents.

16. A sports goggle comprising: a flexible frame comprising an outer surface and an inner surface disposed a distance from the outer surface, the outer surface configured to be oriented away from a user's face and the inner surface configured to conform to a shape of the user's face, the inner surface coupled to the outer surface and spaced apart from the outer surface by a spaced apart region; a lens attached to the flexible frame, wherein the flexible frame is disposed at least partially around an outer periphery of the lens; a plurality of first apertures disposed on the outer surface of the flexible frame; a plurality of second apertures disposed on the inner surface of the flexible frame; a flexible liner provided on the inner surface and configured to contact a users face, the flexible liner disposed directly over the plurality of second apertures; and a plurality of channels formed through the flexible frame, each channel connecting a respective first aperture of the plurality of first apertures to a respective second aperture of the plurality of second apertures through the spaced apart region, and configured to direct airflow from the respective first aperture to the respective second aperture to disperse airflow flowing through the second aperture directly into the flexible liner to cool the user's face where the flexible liner contacts the user's face, wherein at least one first aperture, second aperture, and channel is disposed on a top portion of the flexible frame, and wherein at least one first aperture, second aperture, and channel is disposed on a bottom portion of the flexible frame.

17. A sports goggle comprising: a flexible frame comprising: an outer surface configured to be oriented away from a user's face; an inner surface spaced apart from the outer surface by a spaced apart region, the inner surface configured to conform to a shape of the user's face; a plurality of frame members extending between the outer surface and the inner surface within the spaced apart region to couple the outer surface to the inner surface; a lens attached to the flexible frame, wherein the flexible frame is disposed at least partially around an outer periphery of the lens; a flexible liner provided on the inner surface of the flexible frame and configured to contact the users face; a first aperture disposed on the outer surface of the flexible frame; a second aperture disposed on the inner surface of the flexible frame, wherein the flexible liner is disposed directly over the second aperture to cover the second aperture; and a channel formed through the flexible frame and extending through the space defined between the outer surface and the inner surface, connecting the first aperture to the second aperture through the spaced apart region, and configured to direct airflow from the first aperture to the second aperture to disperse airflow flowing through the second aperture directly into the flexible liner to cool the user's face where the flexible liner contacts the user's face.

* * * * *